US008008356B2

(12) United States Patent
Childs et al.

(10) Patent No.: US 8,008,356 B2
(45) Date of Patent: Aug. 30, 2011

(54) POLYAPHRON DISPERSIONS CONTAINING A COMPLEX INTERNAL PHASE

(75) Inventors: Andrew Childs, Cambridge (GB); Derek Wheeler, Guildford (GB)

(73) Assignee: Drug Delivery Solutions Limited, Letterhead, Surrey (GB)

( * ) Notice: Subject to any disclaimer, the term of this patent is extended or adjusted under 35 U.S.C. 154(b) by 10 days.

(21) Appl. No.: 10/590,668

(22) PCT Filed: Feb. 24, 2005

(86) PCT No.: PCT/GB2005/000659
§ 371 (c)(1),
(2), (4) Date: Aug. 25, 2006

(87) PCT Pub. No.: WO2005/082515
PCT Pub. Date: Sep. 9, 2005

(65) Prior Publication Data
US 2007/0190088 A1    Aug. 16, 2007

(30) Foreign Application Priority Data
Feb. 27, 2004    (GB) .................................. 0404403.8

(51) Int. Cl.
*C09K 3/00* (2006.01)
(52) U.S. Cl. ......................................... 516/10; 424/401

(58) Field of Classification Search .................... 516/10; 424/401
See application file for complete search history.

(56) References Cited

U.S. PATENT DOCUMENTS

| 3,779,907 | A | * | 12/1973 | Li et al. ......................... 210/638 |
| 4,254,105 | A | * | 3/1981 | Fukuda ........................ 514/762 |
| 4,486,333 | A |   | 12/1984 | Sebba |
| 4,999,198 | A | * | 3/1991 | Barnett et al. ................ 424/449 |
| 2004/0002550 | A1 | | 1/2004 | Mercurio |
| 2004/0120975 | A1 | | 6/2004 | Lahanas et al. |

FOREIGN PATENT DOCUMENTS

| WO | 9732559   | 9/1997 |
| WO | 0162214   | 8/2001 |
| WO | 2005011628 | 2/2005 |

OTHER PUBLICATIONS

Menger et al., (Microscopic Observation of a Polyaphron Transforming into a Microemulsion, J. Am. Chem. Soc. 1991, 113, 5119-5120).*

* cited by examiner

*Primary Examiner* — Ling-Siu Choi
*Assistant Examiner* — Chun-Cheng Wang
(74) *Attorney, Agent, or Firm* — Rissman Hendricks & Oliverio LLP

(57) ABSTRACT

A polyaphron dispersion comprising an external phase and polyaphrons having an internal phase, the internal phase comprising (i) a first phase which is liquid and (ii) a second phase which is liquid or gaseous.

19 Claims, No Drawings

POLYAPHRON DISPERSIONS CONTAINING A COMPLEX INTERNAL PHASE

BACKGROUND OF THE INVENTION

1. Field of the Invention

The present invention relates to a polyaphron dispersion.

2. The Prior Art

A polyaphron dispersion is generally also known as a biliquid foam. This phrase is known, for example, from Sebba, F. (Felix), "Foams and biliquid foams, aphrons", 1987. ISBN: 0471916854. Biliquid foams are known in the art and are described in the following literature references by Sebba: "Biliquid foams", J. Colloid and Interface Science, 40 (1972) 468-474; and "The Behaviour of Minute Oil Droplets Encapsulated in a Water Film", Colloid Polymer Sciences, 257 (1979) 392-396.

U.S. Pat. No. 4,486,333 to Sebba describes a particular method for the preparation of biliquid foams by agitating a hydrogen bonded liquid containing a soluble surfactant to produce a gas foam and intermittently adding to the gas foam a non-polar liquid which is immiscible with the hydrogen bonded liquid, the surfactant-containing hydrogen bonded liquid being selected to provide a spreading coefficient equal to or greater than zero.

Known polyaphron dispersions contain a single liquid external phase and a single liquid internal phase. We have now discovered a polyaphron dispersion which can contain additional phases in the internal phase, and a process for the preparation thereof.

SUMMARY OF THE INVENTION

Accordingly, the present invention provides a polyaphron dispersion comprising an external phase and polyaphrons having an internal phase, the internal phase comprising (i) a first phase which is liquid and (ii) a second phase which is liquid or gaseous.

The process for preparing a polyaphron dispersion as defined above comprises (a) forming the internal phase and (b) forming a polyaphron dispersion comprising an external phase and the internal phase prepared in step (a).

The polyaphron dispersion preferably comprises from 70 to 95% by weight of the internal and 5 to 30% by weight of the external, or continuous phase. The external phase is preferably an aqueous phase. It may also be composed of a liquid which has hydrogen bonding such as glycerin, propylene glycol and/or ethanol or a mixture thereof with water. A surfactant to stabilise the dispersion may also be included, for example in an amount of from 0.1 to 3%, preferably 0.1 to 1%, by weight based on the total weight of the dispersion. Suitable surfactants are, for example, anionic, cationic, non-ionic, amphoteric or zwitterionic surfactants, such as sodium lauryl ether sulphates, polyethoxylated castor oil, ethoxylated oleyl alcohols or polyethoxylated hydrogenated castor oils.

The internal phase comprises at least two liquid phases or at least a liquid phase and a gas phase. The internal phase may, of course, also comprise additional phases, such as an additional liquid phase, an additional gas phase or an additional solid phase.

The internal phase may, for example, comprise an aqueous phase and a non-aqueous phase, an emulsion or a biliquid foam (or polyaphron dispersion). The internal phase may also comprise a single aqueous phase and a single non-aqueous phase.

When the internal phase comprises an emulsion, the emulsion is, for example, a water-in-oil emulsion. The continuous phase of the emulsion is immiscible with the external phase of the polyaphron dispersion. The emulsion may, for example, comprise from 10% to 80% of the non-continuous phase and from 20% to 90% of the continuous phase. Either or both of the continuous phase and the non-continuous phase may comprise one or more additives, particularly additives which are incompatible with components of the external phase of the polyaphron dispersion. Examples of suitable oil phases are those mentioned below with respect to the international phase when it is a polyaphron dispersion. An emulsion may be prepared by a standard techniques known in the art, for example by use of a pair heated vessels in which the aqueous and non aqueous phases are prepared prior to final mixing and emulsification by means of a high shear device such as a rotor stator device of the 'Silverson' type.

When the internal phase comprises a biliquid foam or a polyaphron dispersion (which may itself be a complex polyaphron dispersion of the present invention), the external phase may be aqueous or non-aqueous. The external phase of this internal phase is different from the external phase of the polyaphron dispersion of the invention. The internal phase may comprise from 10% to 80% of the non-continuous phase and from 90% to 20% of the continuous phase. Either or both of the continuous phase and the non-continuous phase may comprise one or more additives, particularly additives which are incompatible with components of the external phase of the polyaphron dispersion. Examples of suitable oil phases are oils which are liquid at room temperature (e.g. 20 degrees C.) such as, for example, one or more selected from a cyclomethicone, dimethicone, dimethiconol, dimethicone copolyol, an emollient ester such as isopropyl stearate, lanolate, myristateor palmitate, or octyl palmitate, a glyceride such as avocado oil, coconut oil, soybean oil or sunflower oil, or a caprylic/capric triglyceride, a lanolin oil, mineral oil or natural oil, or oleyl alcohol, or any other oil known to be used in emulsions for whatever purpose. Also included in the definition of oil are water insoluble solvents such as hexane, toluene, benzene, kerosene, diesel oil and other like solvents and water-insoluble organic liquids. The biliquid foam or polyaphron dispersion may be prepared by a standard techniques known in the art, for example by those indicated herein.

When the internal phase comprises a single aqueous phase and a single non-aqueous phase, it may be prepared by forming an unstable emulsion or polyaphron suspension, which is subsequently allowed to separate into two components on standing once the polyaphron suspension of the present invention is fully formed.

The external and/or internal phase of the polyaphron dispersion may, for example, comprise one or more surfactants or other additives. Suitable surfactants for forming and stabilising biliquid foams or polyaphrons can be selected for example, from the list given in WO 97/32559 or will be well-known to those skilled in the art. Methods of producing biliquid foams are described in U.S. Pat. No. 4,486,333 involving the preliminary formation of a gas foam in order to provide a sufficiently large surface area on which the biliquid foam can subsequently be formed. It has been found that the prior formation of a gas foam is not required to manufacture a stable biliquid foam, provided that a suitable stirring mechanism is provided in the manufacturing vessel.

Such an apparatus comprises a tank provided with a stirrer in which the stirrer blade breaks the interface between the liquid and air and provides low shear mixing throughout the whole of the volume of the biliquid foam throughout the whole of the production process. A delivery device is provided through which the internal phase of the dispersion, which in this case comprises at least two liquids, is delivered to the tank. The design of the delivery device is such that the rate of addition of the internal phase fluid can be controlled and varied during the production process. A feature of the production process is that the internal phase is added to the stirred external phase slowly at first until sufficient droplets have been formed to constitute a large, additional surface area for the more rapid formation of new droplets. At this point, the rate of addition of the internal phase may be increased.

The production process preferably comprises the following steps:
1. The addition of one or more chosen surfactants to one or other or both phases (as previously determined by experiment).
2. The charging of the external phase into the bottom of a process vessel.
3. The incorporation of the stirrer into the vessel so that it stirs the surface of the external phase.
4. Adjustment of the stirrer speed to a previously determined level.
5. The slow addition of the internal phase whilst continuing to stir at the prescribed speed.
6. The speeding up of the rate of addition of the internal phase once a prescribed amount (usually between 5% and 10% of the total amount to be added) has been added.

The stirring rate and the rate of addition of the internal phase are variables, the values of which depend upon the detailed design of the manufacturing plant (in particular, the ratio of tank diameter to impeller diameter), the physico-chemical properties of the internal phase and the nature and concentrations of the chosen surfactants. These can all be pre-determined by laboratory or pilot plant experiment.

It will be understood by those skilled in the art that other manufacturing methods for the polyaphron dispersion may be used, as appropriate.

Colloidal gas aphrons are known in the art as, for example, described by Sebba in "Foams and biliquid foams, aphrons", 1987. ISBN: 0471916854. Such colloidal gas aphrons containing a gas such as air, nitrogen, carbon dioxide or a reactive gas such as oxygen or hydrogen may constitute the internal phase of the current invention. Colloidal gas aphrons may be prepared as described in the stated reference or by a sparging process, which may include the use of a porous material through which the gas is injected into a suitably prepared water insoluble medium containing surfactants. Alternatively, the gas may be injected into a water-insoluble medium having a sufficient viscosity and or yield value to prevent the agglomeration of individual gas bubbles until the polyaphron dispersion of the present invention is fully prepared.

In one application of the invention, there is produced a food product such as a rich and creamy yoghurt type food product wherein the external phase is aqueous and may contain water soluble flavours, fruit extracts or particles of fruit, water-soluble colouring agents and the like, whereas the internal phase comprises an edible oil (preferably non fattening) such as olive oil or sunflower oil or avocado oil and an internal water phase which may be as high as 80% of the total internal phase concentration. The total concentration of the complex internal phase may be as high as 95% but is preferably about 90%, at which concentration the product has a rich and creamy appearance and taste because of the high concentration of the internal phase. In this manner is produced a low fat, high water content food product containing about 72-80% water phase.

In another application there is produced a self-heating preparation consisting of two or more chemicals capable of undergoing an exothermic reaction when mixed where at least two of the reactants are water-soluble. In this application, at least one reactant is contained in the internal phase and another in the external continuous phase. The composition is such that the reacts do not mix and do not, therefore, undergo an exothermic reaction until the two aqueous phases are mixed during use. By this means, a self-heating composition such as a cosmetic or pharmaceutical composition, preferably in the form of a cream, may be produced providing the reactants are not harmful to human skin.

In a further application there is produced a composition comprising two or more separate and different complex polyaphrons comprising different internal phases dispersed into the same liquid external phase. The external phase may or may not be polymerised at a later stage. This system could give rise to a multi functional product, whereby each complex bi-liquid foam may contain a different active to perform different tasks upon a different stress. Thus a single formulation could be provided, for example having the ability to change colour permanently once cooled, and a different colour once heated and containing two incompatible drug systems.

We have surprisingly found that at least one of the internal liquid phases is in equilibrium with the external phase such that if the external phase is diluted, the internal phase will begin to release active components contained in it at a controlled rate. Thus, for example compositions containing a hydrogen bonded external phase and at least one hydrogen bonded internal phase can be caused to release an active such as an enzyme from the internal phase by diluting the external phase.

The composition of the present invention can be made, for example, at room temperature and low shear and can thus be very useful for enzymes or condition sensitive actives.

Modification of the viscosity profiles of the internal phases and external phase by viscosity modifiers, known to those skilled in the art, can be adjusted to influence the droplet size and aphron strength during manufacture.

Further examples of use of reacting species separated in the two aqueous phases until used include the formulation of adhesive products wherein at least one hydrogen bonded phase such as an aqueous phase contains a suitable adhesive precursor such as a polymer and the other at least one initiator species.

In a similar manner, the present invention allows there to be used a colour change reaction (such as, for example, a reaction using a pH sensitive dye, such as bromothymol blue on the one hand and an acid or base solution on the other).

In yet a further application, the two aqueous phases may be used to keep separate two materials which are mutually incompatible until the moment of use. An example would be the delivery vehicle for two drugs which would precipitate out of solution when combined together (as might be the case, for example, is one drug was anionic in character and the other cationic).

The present invention is now further described in the following Examples.

EXAMPLES

Preparation of Water in Oil Emulsions

Preparation Example 1

A "water in oil" emulsion was prepared from the following ingredients.

| Ingredients | Weight (g) | % |
|---|---|---|
| Aqueous Phase | | |
| 1% Sodium chloride in demineralised water | 50 | 50 |
| Oil Phase | | |
| Dow Corning 5200 formulation aid | 4.0 | 4.0 |
| Medium viscosity white mineral oil | 46 | 46 |
| Total | 100 | 100 |

The water in oil emulsion was prepared in a 250 ml Beaker with a diameter of 6.5 cm. The aqueous phase was added to the oil phase while being stirred at approximately 2000 rpm for 15 minutes with an impeller of diameter 5.5 cm.

Preparation Example 2

A "water in oil" emulsion was prepared from the following ingredients.

| Ingredients | Weight (g) | % |
|---|---|---|
| Aqueous Phase | | |
| 1% Sodium chloride in demineralised water | 100 | 50.0 |
| Oil Phase | | |
| Dow Corning 5225c formulation aid | 7.40 | 3.70 |
| Phenyl trimethicone | 92.6 | 46.3 |
| Total | 200 | 100 |

The water in oil emulsion was prepared in a 500 ml Beaker with a diameter of 6.5 cm. The aqueous phase was added to the oil phase while being stirred at approximately 4500 rpm for 10 minutes with a rotor stator.

Preparation of Complex Biliquid Foams

Example 1

| Ingredients | Weight (g) | % |
|---|---|---|
| Preparation 1 | 90 | 90 |
| PEG 40 Castor Oil | 1.0 | 1.0 |
| Demineralised water | 8.9 | 8.9 |
| Methyldibromo Glutaronitrile (and) Phenoxyethanol (preservative) | 0.1 | 0.1 |
| Total | 100 | 100 |

The PEG 40 castor oil and the preservative were dissolved into the water in a 250 ml Beaker. Preparation 1 was then added to the beaker dropwise, at first, with a stirrer speed of 350 rpm and an impeller of diameter 5.5 cm. As more of preparation 1 was added, the impeller speed was reduced and the rate of addition increased, until total addition of preparation 1 and a stirrer speed of 150 rpm.

Example 2

| Ingredients | Weight (g) | % |
|---|---|---|
| Preparation 2 | 180 | 90 |
| Laureth-7 | 1.8 | 0.9 |
| Sodium Laureth sulphate | 2.0 | 0.1 |
| Demineralised water | 17.8 | 8.9 |
| Diazolidinyl urea, Iodopropynyl butylcarbamate, Propylene glycol (preservative) | 0.2 | 0.1 |
| | | 100.0 |
| Total | 100 | 100 |

The Laureth-7, sodium laureth sulphate and preservative were added to the water and mixed gently in a 500 ml beaker with a flat bladed stirrer. Preparation 2 was then added to the beaker dropwise, at first, with a stirrer speed of 200 rpm. The stirrer speed was reduced as more of preparation 2 was added.

The invention claimed is:

1. A polyaphron dispersion comprising:
   from about 5% to about 30% by weight based on the total weight of the polyaphron dispersion of an external phase; and
   from about 70% to about 95% by weight based on the total weight of the polyaphron dispersion of polyaphrons having an internal phase, the internal phase comprising:
   (i) a first phase which is liquid, and
   (ii) a second phase which is liquid or gaseous;
   wherein when the internal phase comprises at least two liquid phases, each of the liquid phases is a liquid at room temperature.

2. The polyaphron dispersion according to claim 1, wherein the internal phase comprises at least two liquid phases.

3. The polyaphron dispersion according to claim 1, wherein the internal phase comprises an aqueous phase and a non-aqueous phase.

4. The polyaphron dispersion according to claim 3, wherein the internal phase comprises a single aqueous phase and a single non-aqueous phase.

5. The polyaphron dispersion according to claim 1, wherein the internal phase comprises an emulsion.

6. The polyaphron dispersion according to claim 1 wherein the internal phase comprises polyaphrons.

7. The polyaphron dispersion according to claim 1, wherein the internal phase additionally comprises a solid phase.

8. The polyaphron dispersion according to claim 1, wherein the internal phase comprises at least 60 wt. % of an aqueous phase.

9. The polyaphron dispersion according to claim 1, wherein a component of the external phase is capable of reacting with a component of the internal phase upon the polyaphrons being disrupted or destroyed.

10. A process for preparing a polyaphron dispersion as defined in claim 1, which comprises:
    a. forming the internal phase; and
    b. forming a polyaphron dispersion comprising an external phase and the internal phase prepared in step a.

11. The polyaphron dispersion according to claim 1, wherein the external phase is aqueous.

12. The polyaphron dispersion according to claim 1, wherein the second phase is gaseous and the internal phase additionally comprises a solid phase.

13. A polyaphron dispersion comprising:
from about 5% to about 30% by weight based on the total weight of the polyaphron dispersion of an external phase; and
from about 70% to about 95% by weight based on the total weight of the polyaphron dispersion of polyaphrons having an internal phase, the internal phase comprising:
(i) a first phase which is liquid, and
(ii) a second phase which is liquid or gaseous;
wherein when the internal phase comprises at least two liquid phases, each of the liquid phases is a liquid at room temperature,
wherein the internal phase comprises polyaphrons.

14. The polyaphron dispersion according to claim 13, wherein the external phase is aqueous.

15. The polyaphron dispersion according to claim 13, wherein the internal phase comprises at least two liquid phases.

16. The polyaphron dispersion according to claim 13, wherein the internal phase comprises an aqueous phase and a non-aqueous phase.

17. A polyaphron dispersion comprising:
from about 5% to about 30% by weight based on the total weight of the polyaphron dispersion of an external phase; and
from about 70% to about 95% by weight based on the total weight of the polyaphron dispersion of polyaphrons having an internal phase, the internal phase comprising:
(i) a first phase which is liquid, and
(ii) a second phase which is liquid or gaseous;
wherein when the internal phase comprises at least two liquid phases, each of the liquid phases is a liquid at room temperature,
wherein the internal phase comprises at least 60 wt. % of an aqueous phase.

18. The polyaphron dispersion according to claim 17, wherein the external phase is aqueous.

19. The polyaphron dispersion according to claim 17, wherein the internal phase comprises at least two liquid phases.

* * * * *